United States Patent
Kass et al.

Patent Number: 5,482,829
Date of Patent: Jan. 9, 1996

[54] COMPOSITION AND METHOD FOR ENRICHMENT OF WHITE BLOOD CELLS FROM WHOLE HUMAN BLOOD

[75] Inventors: Lawrence Kass, Hinckley, Ohio; Leonard Spolter, Granada Hills, Calif.

[73] Assignee: International Remote Imaging Systems, Inc., Chatsworth, Calif.

[21] Appl. No.: 361,104

[22] Filed: Dec. 21, 1994

Related U.S. Application Data

[62] Division of Ser. No. 52,504, Apr. 26, 1993, Pat. No. 5,397,479.

[51] Int. Cl.⁶ .............................. C02F 1/54; C02F 1/56
[52] U.S. Cl. ................. 435/2; 435/13; 530/419; 530/421; 530/830; 210/728; 210/730
[58] Field of Search ........................ 530/419, 420, 530/421, 850; 435/2, 13; 210/728, 729, 730, 731

[56] References Cited

U.S. PATENT DOCUMENTS

| | | |
|---|---|---|
| 4,181,609 | 1/1980 | Wardlaw et al. |
| 4,255,256 | 3/1981 | Ferrante et al. .................. 210/730 |
| 4,663,058 | 5/1987 | Wells et al. ..................... 210/801 |
| 4,765,899 | 8/1988 | Wells et al. ..................... 210/519 |
| 4,968,432 | 11/1990 | Antwiler ......................... 210/728 |
| 5,118,428 | 6/1992 | Sand et al. ...................... 210/749 |

*Primary Examiner*—Neil McCarthy
*Attorney, Agent, or Firm*—Limbach & Limbach

[57] ABSTRACT

A composition and method for separating red blood cells from whole blood comprising a rouleaux-forming aggregator and an enhancer for enhancing the settling rate. The enhancer is a material which alters directly or indirectly the properties of the red blood cell and may alter the structure and/or reactivity of the aggregator, without adversely affecting the morphology and function of white blood cells. In most instances, the red blood cell enhancers of the invention are osmotic agents. Such agents create a hypertonic solution while not entering the cells themselves. Preferably the enhancer is a salt of oxalic acid, a salt of malonic acid, mannitol or sucrose. Potassium oxalate is most preferred. High molecular weight substances which are large enough to form molecular bridges between red blood cells form the aggregators used in the invention. Examples of useful aggregators include dextran, hespan, pentaspan, ficoll, gum arabic, polyvinylpyrrolidone, nucleic acids, and proteins such as fibrinogen and gamma globulins.

25 Claims, 5 Drawing Sheets ns: 5,482,829

COMPOSITION AND METHOD FOR ENRICHMENT OF WHITE BLOOD CELLS FROM WHOLE HUMAN BLOOD

This is a divisional of application Ser. No. 08/052,504, filed Apr. 26, 1993, now U.S. Pat. No. 5,397,479.

FIELD OF THE INVENTION

This invention relates to the separation of red blood cells from whole blood. In particular, the invention relates to a method and composition for increasing the sedimentation rate of red blood cells in a whole blood specimen.

DESCRIPTION OF THE RELEVANT ART

Whole blood consists of various particulate constituents including white blood cells, red blood cells, and platelets. It is frequently necessary to separate red blood cells from whole blood in order to analyze the other blood components. Gravity sedimentation and centrifugation are known methods of separating the other blood components from red cells.

Certain substances have been found to accelerate the separation of red blood cells from the other components of whole blood. These substances are herein referred to as "aggregators." Aggregators form molecular bridges between red blood cells. The bridges reduce the distance between the red blood cells, thereby reducing the effect of the normal repulsive forces (zeta potential) between these cells. Once the repulsive forces of the negatively charged groups of the red blood cell surface have been overcome, the adsorptive forces of the highly lipoidal red blood cell surface strongly hold adjacent cells together. Bridging causes the red blood cells to aggregate into large masses, called rouleaux, which sediment more rapidly than individual red blood cells.

Materials which are known to act as aggregators include synthetic and natural polysaccharides, proteins, and other natural and synthetic polymers one example of a known aggregator is high molecular weight dextran, a glucose polymer.

The analysis of certain components in whole blood could be accelerated if blood components were separated more rapidly than by methods currently available.

SUMMARY OF THE INVENTION

In order to achieve rapid separation of blood components, the present invention identifies methods and compositions which increase the effectiveness of aggregating agents, thereby increasing red blood cell settling rates in whole blood. The invention is further directed to a composition and method for separating red blood cells from whole blood comprising a rouleaux-forming aggregating agent and a dehydrating osmotic enhancer for enhancing the settling rate. This dehydrating osmotic enhancer is preferably selected from the group consisting of salts of oxalic acid, salts of malonic acid, mannitol and sucrose, and is most preferably potassium oxalate or potassium malonate.

In the method of the invention, a sample of whole blood is added to a solution which includes the red blood cell aggregator and enhancer composition of the invention, and red blood cells are allowed to aggregate and settle. Use of the invention results in a significant increase in red blood cell sedimentation rate compared with the rate which is measured for either the aggregator or enhancer alone.

BRIEF DESCRIPTION OF THE DRAWINGS

The invention will be better understood by reference to the appended Figures. The effect of aggregators, enhancers, and various combinations of aggregators and enhancers on red blood cell settling are shown. The ordinate of each of these graphs represents the height of the leukocyte-rich plasma (LRP) and the abscissa represents time after mixing of the blood and aggregator-enhancer solutions.

DETAILED DESCRIPTION OF THE INVENTION

For some years it has been known that certain polysaccharides such as dextran and certain proteins such as fibrinogen and gamma globulins can agglutinate red blood cells and thereby accelerate their sedimentation in a sample of blood. The present invention relates to significant improvement in the use of such aggregators.

A number of alternative embodiments exist for the present invention. Each embodiment of the inventive composition includes a combination of an aggregator and an enhancer. The method of the invention includes the step of combining the aggregator-enhancer combination with whole blood.

Figure 2:
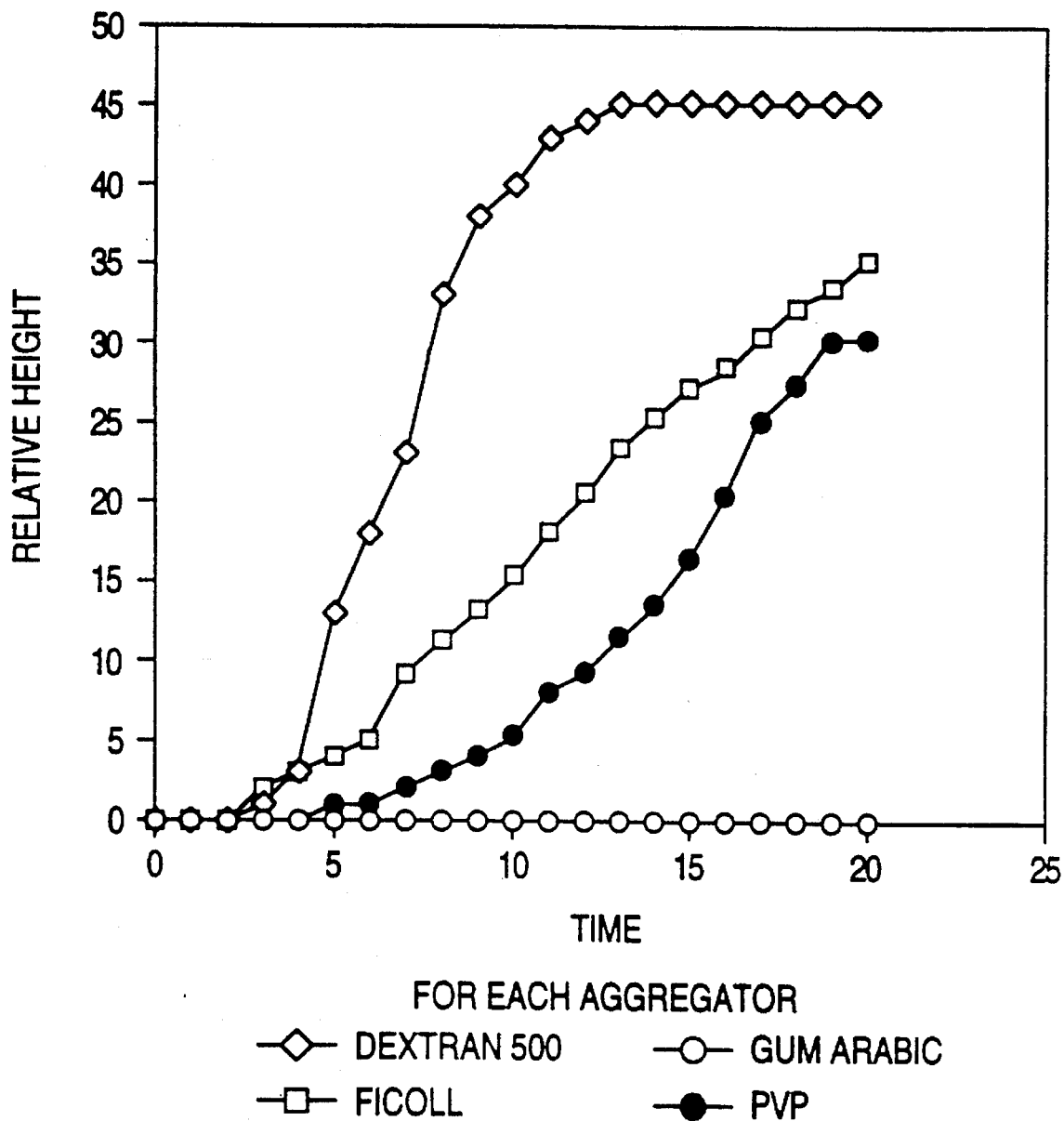
FIG. 2 shows the rate of settling for certain aggregators without any enhancer present.

In the invention, aggregators typically are high molecular weight substances which are large enough to form molecular bridges between red blood cells. Examples of appropriate aggregators include natural polymers, synthetic polymers derived from natural or synthesized monomers, polysaccharides such as relatively high molecular weight dextrans (T70 through T2000, a series of dextran polymers available from Pharmacia LKB Biotechnology AB, Upsula, Sweden, the number indicating the average molecular weight of the dextran in thousands), hespan, pentaspan, ficoll, gum arabic, polyvinylpyrrolidone, nucleic acids, and large molecular weight proteins such as fibrinogen and gamma globulins. The effect of some of these aggregators on red blood cell sedimentation is shown in FIG. 2.

The key features that an aggregator should possess which will permit its successful use in the present invention are large molecular size and the presence of functional groups which can interact with the red cell membrane on cell surface receptors, such as lectin-like sites on the membrane. Such groups include, but are not limited to, sites specific for the carbohydrate moieties of dextran, hespan, pentaspan and ficoll, and sites specific for certain amino acids.

The concentration of aggregator to achieve aggregation sufficient to promote settling can readily be selected. Aggregators can effectively promote red blood cell aggregation over a broad concentration range. However, aggregation rate may be decreased if the aggregator concentration is either too high or too low. If the aggregator concentration is excessive, all of the available binding sites on the surface of the red cells will be occupied by one end of the aggregator molecule and no binding sites on other red cells will be available for the other end of the bound aggregator. Thus, cross-linking of the red cells to form rouleaux is not possible. If the aggregator concentration is too low, the number of aggregator molecules available for formation of cross-links between red cells is not sufficient to promote the formation of rouleaux. As the aggregator concentration is increased, greater numbers of aggregator molecules can form links between red blood cells to promote rouleaux formation. In a preferred embodiment, a 6% solution of the aggregator in saline is used where the proportion of blood to aggregator solution is 4:1. This aggregator concentration and proportion of aggregator solution to blood were chosen in order to obtain rapid settling while minimizing dilution of blood components.

Figure 3:
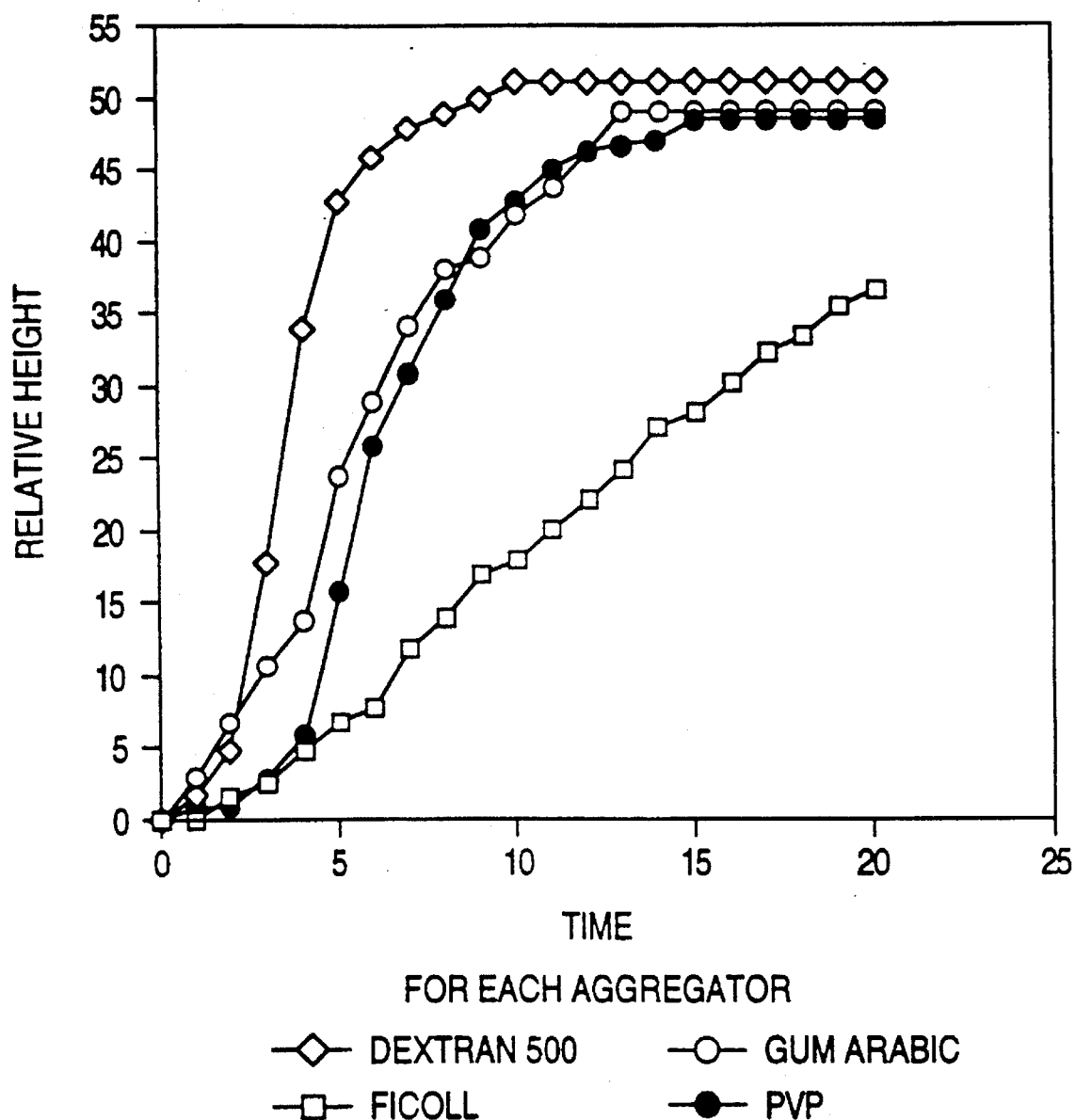
FIG. 3 shows the effect of combinations of the aggregators in FIG. 2 with the enhancer potassium oxalate on the rate of settling of red blood cells.

For the purposes of this invention, the enhancer is a material which alters directly or indirectly the properties of the red blood cell and may alter the structure and/or reactivity of the aggregator. A suitable enhancer should not adversely affect the morphology and function of white blood cells. In most instances, the red blood cell enhancers of the invention are osmotic agents. They create a hypertonic solution while not entering the cells themselves. This results in the removal of water from the red blood cells, thereby decreasing their buoyant-density. The effect of the combination of gum arabic and potassium oxalate on red blood cell settling involves an action on the aggregator as well as on the red blood cells (FIGS. 2 and 3). The additional action of the oxalate in this latter case involves the removal of polyvalent cations from the gum arabic molecule. This causes unfolding of the gum arabic molecule enabling interaction of this molecule with binding sites on different red blood cells, thereby promoting rouleaux formation.

Figure 1:
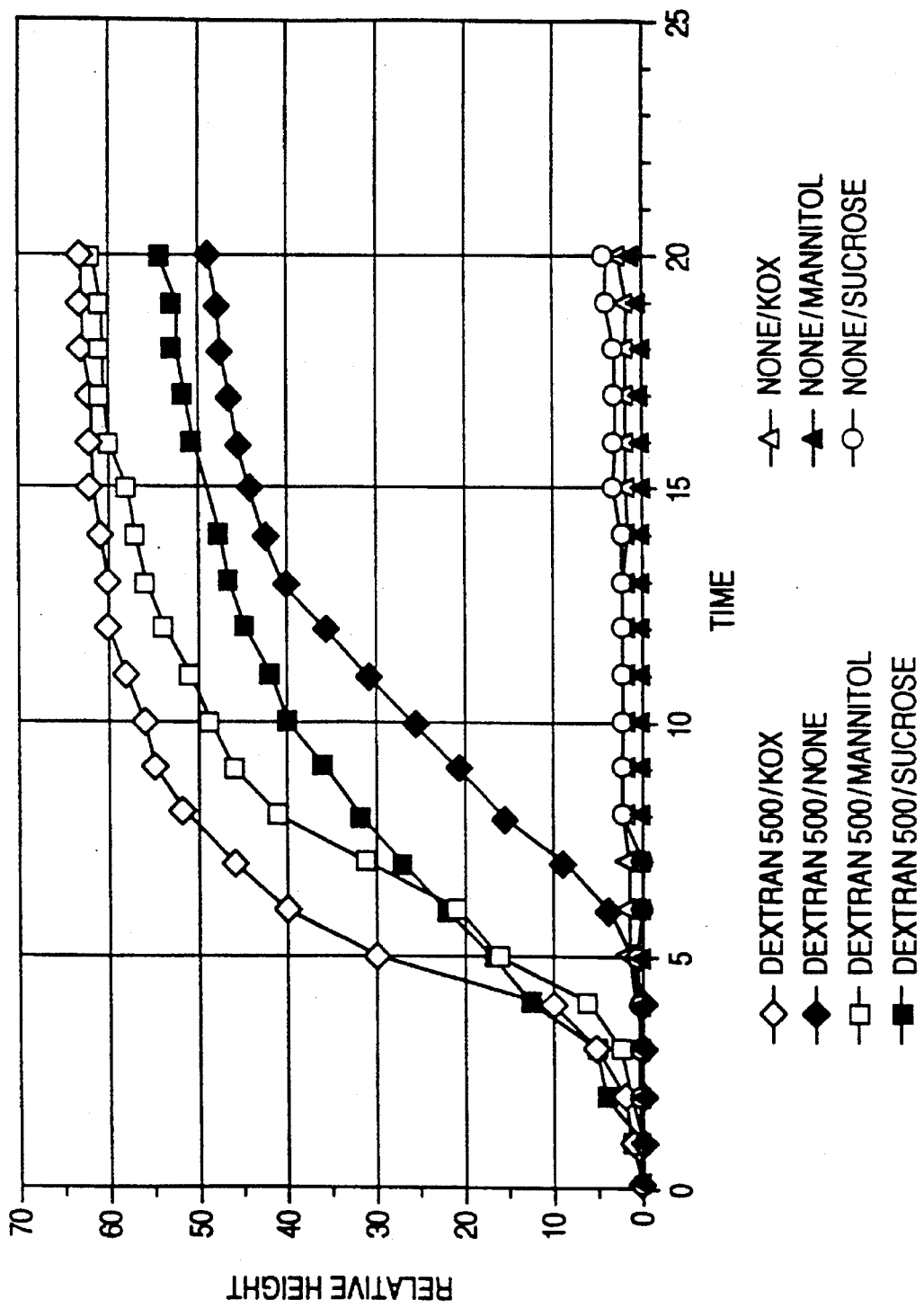
FIG. 1 shows the effect of combinations of several enhancers (potassium oxalate, mannitol and sucrose) and the aggregator, Dextran T500, on the rate of settling of red blood cells.
Figure 4:
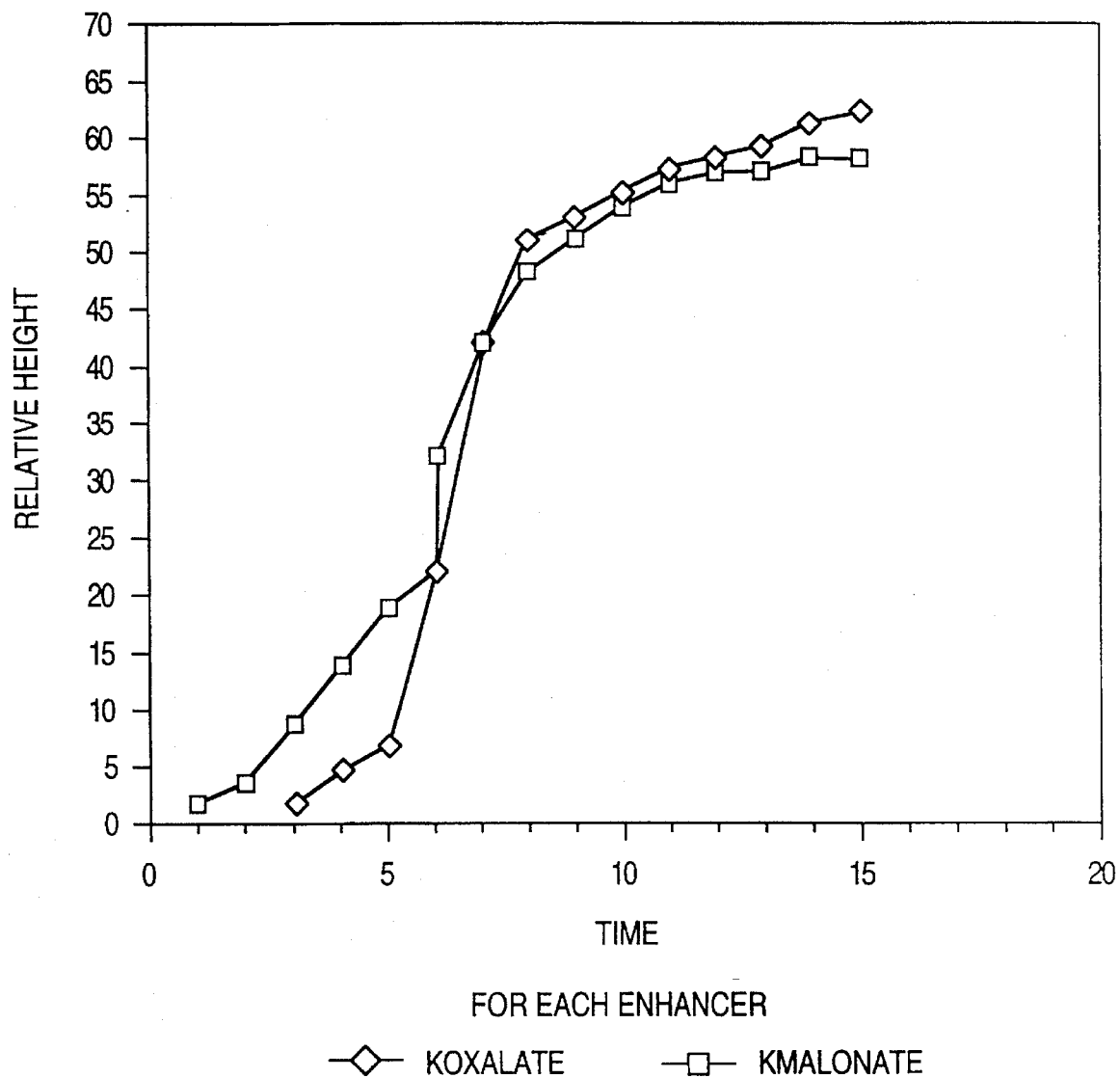
FIG. 4 shows the similarity of effect of each of the enhancers potassium oxalate and potassium malonate when each is combined with the aggregator Dextran T500, on the settling of red blood cells.

Examples of acceptable enhancers for the invention include soluble salts of oxalate and malonate, as well as mannitol, and sucrose. In a preferred embodiment, potassium oxalate is used. The combination of potassium oxalate and Dextran T500 (MW 500,000) was found to yield the most satisfactory red blood cell sedimentation system (FIGS. 1 and 3). Potassium malonate and Dextran T500 together also provide an enhanced settling rate (FIG. 4).

Method For Study of Effect of Aggregators and Enhancers on Red Blood Cell Sedimentation.

The experiments from which the data shown in the Figures were derived were conducted as follows. One volume of settling solution and four volumes of peripheral venous blood, anticoagulated with EDTA, were added to a 10×75 mm glass test tube. The blood and settling solution were mixed and transferred to an upright Wintrobe tube, maintained at room temperature. The height of the settling red blood cells in the Wintrobe tube was recorded for up to twenty minutes.

The composition of the settling solution may be varied. The aggregator component may be comprised of the following substances, each made as a 6% solution in saline with 0.32M potassium oxalate: Dextran T500, ficoll, polyvinylpyrrolidone (PVP), and gum arabic, as examples of a wide range of aggregating agents with different physicochemical properties (FIG. 3).

The most satisfactory system for sedimentation of erythrocytes was the mixture of four volumes of whole blood and one volume of the settling solution Composed of 6% Dextran T500 and 0.32M potassium oxalate. The addition of the mixture of this aggregator and enhancer caused acceleration over what could be obtained with the aggregator or enhancer alone (FIG. 1). As can be seen, both the time at which settling begins and the degree of settling are much improved using the combination. Similar effects of potassium oxalate were found for other aggregators (FIG. 3).

In the settling solutions used in the experiment shown in FIGS. 1 and 4, the concentration of the Dextran T500 used as the aggregating agent was 6% in saline, the concentration of potassium oxalate or potassium malonate was 0.32M, and the concentration of mannitol or sucrose as the enhancer was 0.96M. The similarity of effect of each of these enhancers, which do not enter the red blood cells and which have different physicochemical properties, on the rate of settling of Dextran T500 agglutinated red blood cells indicates that they are acting as osmotic agents. The lower concentration limit of these enhancers is that concentration required to generate a hypertonic solution when the settling solution is added to the blood. The greater the enhancer concentration, the greater the osmotic effect. The upper limit of the enhancer concentration is determined by the solubility of the enhancer, the viscosity of the enhancer solution, and any adverse effects that excessively high enhancer levels may have on the blood components being studied.

As seen in FIG. 1, potassium oxalate is a more effective enhancer than either sucrose or mannitol. The similarity of effect of potassium oxalate and potassium malonate is demonstrated in FIG. 4. When used alone without an aggregating agent, potassium oxalate caused little if any acceleration of red blood cell sedimentation (FIG. 1). Analysis of the supernatant obtained after sedimentation was completed, in each of the instances, revealed that it contained predominantly leukocytes and platelets, with occasional individual erythrocytes and a few aggregates of erythrocytes. The leukocytes displayed differential coloration when stained supravitally with Basic Orange 21 (C.I. 48035). Applicable staining techniques are described in U.S. Pat. Nos. 4,615,878, 4,581,223, 4,500,509 and 4,400,370, the contents of each of which are hereby incorporated by reference. This stainability indicated that the cells were viable and altered little, if any, by exposure to the various settling solutions.

Figure 5:
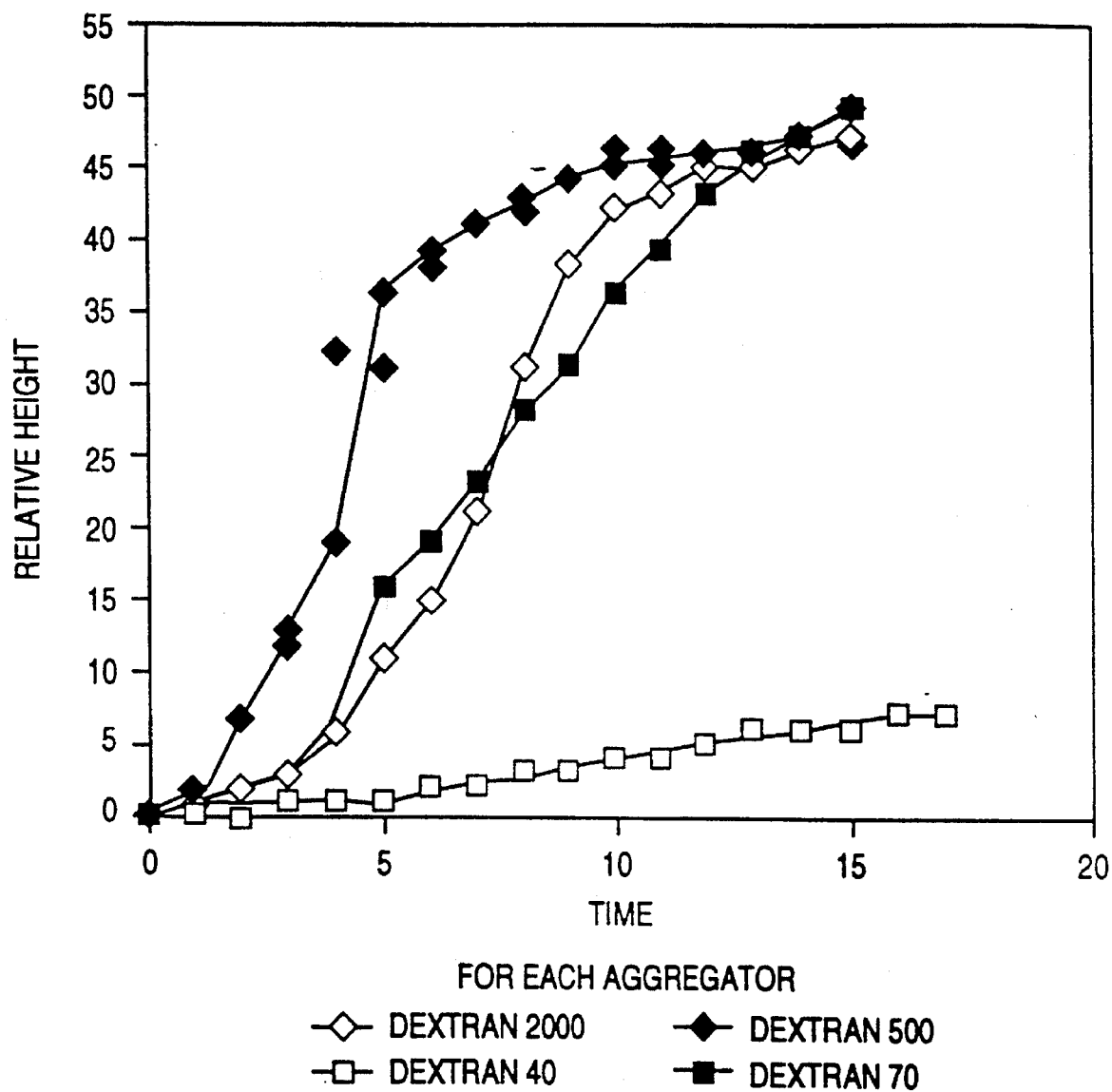
FIG. 5 compares the effect of molecular size of various dextran polymers on settling rate.

FIG. 5 shows the effect of molecular size on the effectiveness of a dextran-potassium oxalate settling solution. As can be seen, Dextran T40 (MW approx. 40,000) produced poor results while Dextran T70, Dextran T500 and Dextran T2000 all performed better. Thus, it is preferred that the aggregator used in the invention have a molecular weight of more than about 40,000.

While the present invention has been described by reference to the preferred embodiments, those skilled in the art will understand that many variations of these embodiments are possible without departing from the fundamental character of the invention. It is therefore considered that such variations fall within the scope of the invention, and the appended claims.

What is claimed is:

1. A composition for separating blood cells from a solution containing said cells, comprising a settling solution which comprises dextran having a molecular weight greater than about 40,000 and a settling rate enhancer member selected from the group consisting of potassium oxalate, potassium malonate, mannitol and sucrose, wherein the amounts of said dextran and said settling rate enhancer are sufficient to increase red blood cell sedimentation rate compared with the rate which is measured for either the dextran or enhancer alone and wherein said enhancer does not adversely affect the morphology and function of white blood cells.

2. A composition for separating red blood cells, comprising a settling solution which comprises a rouleaux forming aggregator selected from the group consisting of synthetic polymers, polysaccharides, proteins, and nucleic acids and a settling rate enhancer, wherein the amounts of said aggregator and said settling rate enhancer are sufficient to increase red blood cell sedimentation rate compared with the rate which is measured for either the aggregator or enhancer alone and wherein the enhancer does not adversely affect the morphology and function of white blood cells.

3. A composition as in claim 2 wherein said rouleaux forming aggregator is selected from the group consisting of dextran, hespan, pentaspan, ficoll, gum arabic, polyvinylpyrrolidone, gamma globulin, and fibrinogen.

4. A composition as in claim 1 wherein said rouleaux forming aggregator is dextran having a molecular weight of about 70,000 or greater.

5. A composition as in claim 2 wherein said enhancer is selected from the group consisting of salts of oxalic acid, salts of malonic acid, mannitol and sucrose.

6. A composition as in claim 1 wherein said member is potassium malonate.

7. A composition as in claim 2 wherein said aggregator is polyvinylpyrrolidone, gum arabic or ficoll and said enhancer is potassium oxalate.

8. A composition as in claim 1 wherein said member is potassium oxalate.

9. A composition for separating red blood cells from whole blood, comprising a rouleaux forming aggregator selected from the group consisting of dextran having a molecular weight greater than about 40,000, gum arabic ficoll, and polyvinylpyrrolidone, a solution containing a settling rate enhancer for increasing the settling rate of said cells compared with the rate which is measured for either the aggregator or enhancer alone and wherein said enhancer does not adversely affect the morphology and function of white blood cells.

10. A composition as in claim 9 wherein said aggregator is dextran having a molecular weight of about 500,000.

11. A composition as in claim 9 wherein said enhancer comprises mannitol.

12. A composition as in claim 9 wherein said enhancer comprises sucrose.

13. A composition as in claim 9 wherein said enhancer comprises a salt of oxalic acid.

14. A composition as in claim 9 wherein said enhancer comprises a salt of malonic acid.

15. A composition as in claim 13 wherein said enhancer is potassium oxalate.

16. A composition as in claim 14 wherein said enhancer is potassium malonate.

17. A composition as in claim 10 wherein said enhancer comprises mannitol.

18. A composition as in claim 10 wherein said enhancer comprises sucrose.

19. A composition as in claim 10 wherein said enhancer comprises a salt of oxalic acid.

20. A composition as in claim 10 wherein said enhancer comprises a salt of malonic acid.

21. A composition as in claim 19 wherein said enhancer is potassium oxalate.

22. A composition as in claim 20 wherein said enhancer is potassium malonate.

23. A composition for separating red blood cells, comprising a settling solution, the settling solution comprising a first aggregator component selected from the group consisting of hespan, pentaspan, gamma globulin and fibrinogen and a second settling rate enhancer component selected from the group consisting of a salt of malonic acid, a salt of oxalic acid, mannitol and sucrose wherein the amounts of said aggregator and said settling rate enhancer are sufficient to increase red blood cell sedimentation rate compared with the rate which is measured for either the aggregator or enhancer alone and the enhancer does not adversely affect the morphology and function of white blood cells.

24. The composition of claim 23 wherein said second component is potassium malonate.

25. The composition of claim 23 wherein said second component is potassium oxalate.

* * * * *